United States Patent
Molla et al.

(10) Patent No.: US 12,146,406 B2
(45) Date of Patent: Nov. 19, 2024

(54) FLUID TYPE IDENTIFICATION FROM DOWNHOLE FLUID ANALYSIS USING MACHINE LEARNING TECHNIQUES

(71) Applicant: Schlumberger Technology Corporation, Sugar Land, TX (US)

(72) Inventors: Shahnawaz Hossain Molla, Watertown, MA (US); Farshid Mostowfi, Lexington, MA (US); John Nighswander, Katy, TX (US); Adriaan Gisolf, Bucharest (RO); Kai Hsu, Sugar Land, TX (US); Shunsuke Fukagawa, Kanagawa (JP); Thomas Pfeiffer, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 435 days.

(21) Appl. No.: 17/755,090

(22) PCT Filed: Oct. 22, 2020

(86) PCT No.: PCT/US2020/056811
§ 371 (c)(1),
(2) Date: Apr. 21, 2022

(87) PCT Pub. No.: WO2021/081174
PCT Pub. Date: Apr. 29, 2021

(65) Prior Publication Data
US 2022/0349302 A1   Nov. 3, 2022

Related U.S. Application Data

(60) Provisional application No. 62/924,196, filed on Oct. 22, 2019.

(51) Int. Cl.
*E21B 49/08* (2006.01)
*G01N 21/31* (2006.01)
*G01N 33/28* (2006.01)

(52) U.S. Cl.
CPC .......... *E21B 49/081* (2013.01); *G01N 21/31* (2013.01); *G01N 33/2823* (2013.01); *E21B 2200/22* (2020.05)

(58) Field of Classification Search
USPC .......................................................... 702/6
See application file for complete search history.

(56) References Cited

U.S. PATENT DOCUMENTS 7,586,087 B2   9/2009   Dong et al.
7,966,273 B2   6/2011   Hegeman et al.
(Continued)

FOREIGN PATENT DOCUMENTS

EP   1865147 A1   12/2007
WO   2014200861 A1   12/2014

OTHER PUBLICATIONS

Extended Search Report issued in European Patent Application No. 20878322.5 dated Oct. 11, 2023, 7 pages.
(Continued)

*Primary Examiner* — Paul D Lee
(74) *Attorney, Agent, or Firm* — Jeffrey D. Frantz

(57) ABSTRACT

Embodiments present a method for fluid type identification from a downhole fluid analysis that uses machine learning techniques that are trained and derived from a computer model using pressure, temperature and downhole optical characteristics of sampled fluid.

14 Claims, 10 Drawing Sheets

(56) References Cited

U.S. PATENT DOCUMENTS

| | | | |
|---|---|---|---|
| 8,434,356 B2 | 5/2013 | Hsu et al. | |
| 9,109,434 B2 | 8/2015 | Indo et al. | |
| 9,334,729 B2 | 5/2016 | Indo et al. | |
| 2003/0182061 A1 | 9/2003 | Ferworn et al. | |
| 2009/0030858 A1 | 1/2009 | Hegeman et al. | |
| 2009/0306897 A1 | 12/2009 | Dong et al. | |
| 2013/0103627 A1 | 4/2013 | Maddinelli et al. | |
| 2015/0204189 A1* | 7/2015 | Indo | G01N 21/359 356/440 |
| 2015/0292324 A1 | 10/2015 | Jackson et al. | |
| 2016/0032719 A1 | 2/2016 | Chen et al. | |
| 2017/0370214 A1 | 12/2017 | Wang et al. | |
| 2018/0171769 A1* | 6/2018 | Gu | E21B 43/267 |
| 2018/0299375 A1* | 10/2018 | Young | G06N 5/01 |
| 2018/0320517 A1 | 11/2018 | Indo et al. | |
| 2018/0335538 A1 | 11/2018 | Dupont et al. | |
| 2018/0371905 A1 | 12/2018 | Chen et al. | |
| 2019/0120049 A1* | 4/2019 | Chen | E21B 47/12 |

OTHER PUBLICATIONS

Indo, K., K. Hsu, and J. Pop, Estimation of Fluid Composition From Downhole Optical Spectrometry. SPE Journal, 2015. 20(06): p. 1326-1338.

Dong, C., et al., New Downhole-Fluid-Analysis Tool for Improved Reservoir Characterization. SPE Reservoir Evaluation Engineering, 2008. 11(6): p. 1107-1116.

International Search Report and Written Opinion issued in the PCT Application PCT/US2020/056811, dated Feb. 2, 2021 (11 pages).

Zuo, J.Y., et al., Equation-of-State-Based Downhole Fluid Characterization. 2011, SPE 114702, (10 pages).

International Search Report and Written Opinion issued in PCT Application PCT/US2020/056821, dated Jan. 25, 2021 (10 pages).

James, G., et al., An Introduction to Statistical Learning with Applications in R. Springer Texts in Statistics. 2013: Springer-Verlag New York, pp. 15-36.

Hastie, T., R. Tibshirani, and J. Friedman, The Elements of Statistical Learning. Springer Series in Statistics. 2009: Springer-Verlag New York. 745, pp. 389-403.

Hastie, T., R. Tibshirani, and J. Friedman, The Elements of Statistical Learning. Springer Series in Statistics. 2009: Springer-Verlag New York. 745, pp. 18-32.

International Preliminary Report on Patentability issued in PCT Application No. PCT/US2020/056811 dated May 5, 2022, 6 pages.

International Preliminary Report on Patentability issued in PCT Application No. PCT/US2020/056821 dated May 5, 2022, 7 pages.

\* cited by examiner

FLUID TYPE IDENTIFICATION FROM DOWNHOLE FLUID ANALYSIS USING MACHINE LEARNING TECHNIQUES

CROSS-REFERENCE TO RELATED APPLICATIONS

The present application is a National Stage Entry of International Application No. PCT/US2020/056811, filed Oct. 22, 2020, which claims priority to United States Provisional Application 62/924,196 dated Oct. 22, 2019, the entirety of which is incorporated by reference.

FIELD OF THE DISCLOSURE

Aspects of the disclosure relate to fluid analysis for downhole applications. More specifically, aspects of the disclosure relate to fluid-type identification from downhole fluid analysis data using machine learning techniques.

BACKGROUND

Traditionally, oil and gas companies seek to find, assess, produce and sell fluids, such as natural gas and oil. Starting from exploration to production, oilfield service companies help oil and gas companies measure and quantify the uncertainty associated with the value of their product, namely, reservoir fluids. Through these measurements, useful information is generated about the reservoir fluid in every step.

In subsurface condition, conventional techniques use a Downhole Fluid Analyzer (DFA) tool to measure basic fluid composition of the formation fluid at reservoir pressure and temperature and use these measurements to identify the fluid type and predict gas-oil-ratio of the fluid. FIG. 1A shows a schematic of a tool-string with the fluid analysis module that is known in the art. The measurements taken by such a tool-string can play a crucial role in ensuring that the formation fluid sample collected downhole has minimum level of contamination. The composition is inferred by measuring the optical information of the formation fluid using a downhole spectrometer as presented in FIG. 1B. Additionally, the pressure, temperature, density and viscosity of the fluid is concurrently measured.

There is a need to provide an apparatus and methods that provide a workflow wherein the measurements described above may be used to estimate other physical properties of the formation fluid that cannot be directly measured.

There is a further need to provide a capability to build a preliminary model of reservoir fluid during exploration phases of a project.

There is a still further need to reduce economic costs associated with operations and apparatus described above for finding and analyzing fluids by oil field service companies.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In one non-limiting embodiment, a method is disclosed. The method may comprise collecting optical spectral data for a downhole fluid. The method may also comprise providing the collected optical spectral data to a trained classification module. The method may also comprise processing the collected optical spectral data with the trained classification module configured to determine a fluid type classification. The method may also comprise determining a fluid type based upon the classification based upon the trained classification module.

In another example embodiment, a method is disclosed. The method comprises collecting optical data related to a downhole fluid and extracting data from the collected optical data to form a qualified dataset. The method may also provide for partitioning the qualified dataset to determine a portion of the qualified dataset related to testing data and a second portion of the qualified dataset related to training data. The method may also provide for performing a classification model training on the second portion of the qualified dataset related to the training data, resulting in a trained classification model.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not to be considered limiting of its scope, for the disclosure may admit to other equally effective embodiments.

Figure 1A:
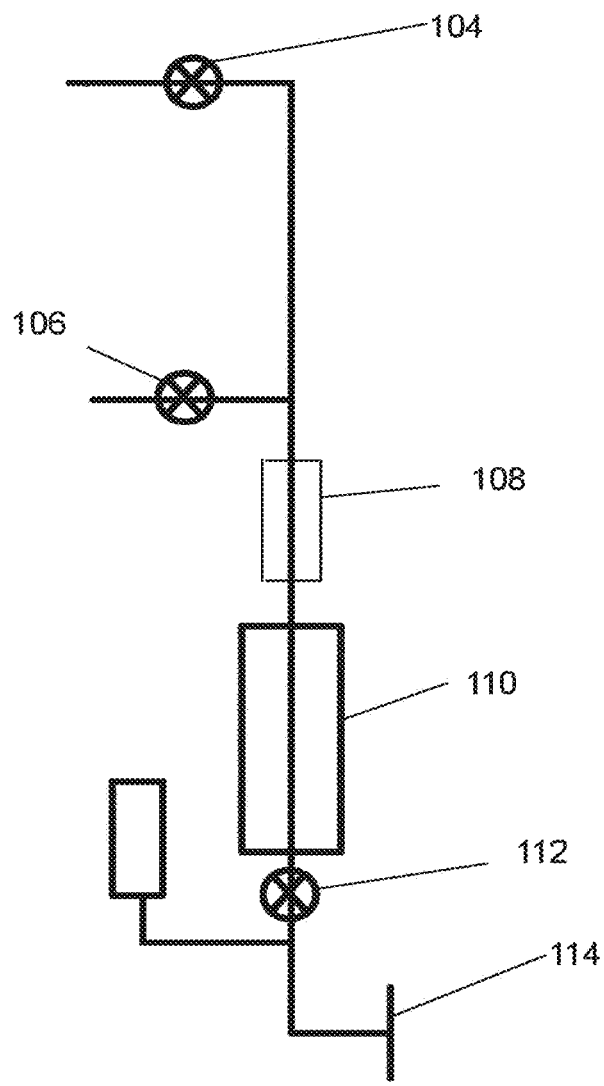
FIG. 1A is a schematic of a tool-string with a fluid analysis module used in conventional methods.

To facilitate understanding, identical reference numerals have been used, where possible, to designate identical elements that are common to the figures ("FIGS"). It is contemplated that elements disclosed in one embodiment may be beneficially utilized on other embodiments without specific recitation.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and should not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and/or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

In subsurface conditions, embodiments of the disclosure provide for a Downhole Fluid Analyzer (DFA) tool to measure basic fluid composition of the formation fluid at reservoir pressure and temperature and use these measurements to identify the fluid type and predict gas-oil-ratio of the fluid. Referring to FIG. 1A a schematic of a tool-string is illustrated with the fluid analysis module. These measurements play a crucial role in ensuring that the formation fluid sample collected downhole has minimum level of contamination. The tool-string has a DFA tool 110 that is configured with sensors to measure fluid compositions of formation fluids while in a wellbore. A probe 114 is positioned to allow for the fluids to be drawn in to the DFA tool 110 through actuation of an isolation valve 112. The isolation valve 112 may be opened and closed remotely by an operator, in some embodiments. A pump 108 is provided to allow for a suction to be created at the probe 114. In embodiments, the pump 108 may be controlled by an operator. Power to the pump 108 may be provided from an uphole power supply, a series or batteries or through a mud turbine, in non-limiting embodiments. A second isolation valve 106 is provided to allow for a fluid entry path to the wellbore. A third isolation valve 104 is also provided for connection to the wellbore.

Figure 1B:
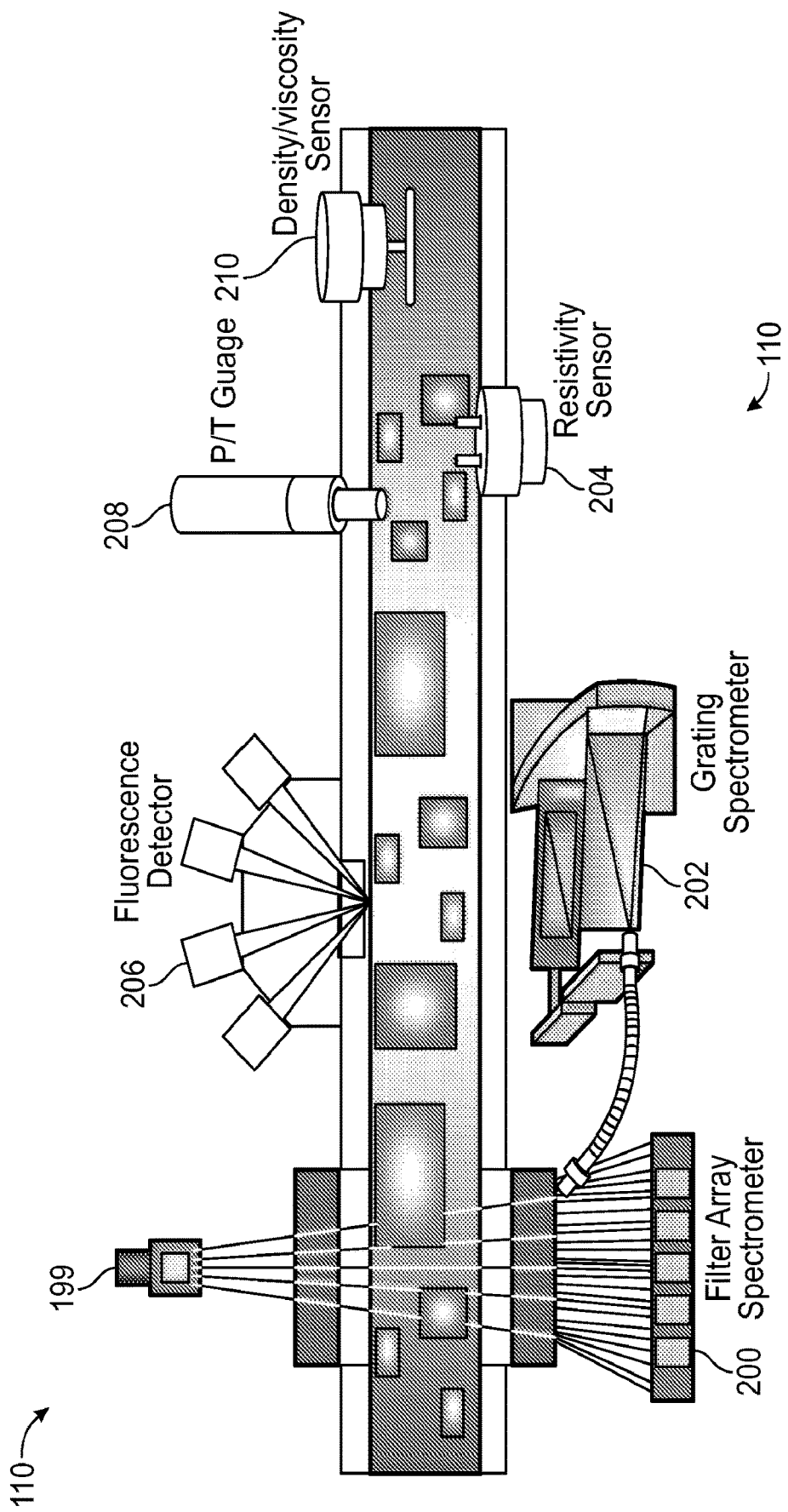
FIG. 1B is a schematic of a downhole spectrometer used to measure optical properties of a downhole fluid.

Referring to FIG. 1B, a system 199 is provided for analyzing formation fluid from within the wellbore. The system 199 may comprise a filter array spectrometer 200, a grating spectrometer 202, a resistivity sensor 204, a fluorescence detector 206, a P/T gauge 208 and a density/viscosity sensor 210. These systems may be independently or simultaneously controlled to analyze fluids sampled from the probe 114. These components, in one embodiment, are located in one downhole arrangement, namely the DFA tool 110. The composition is inferred by measuring the optical information of the formation fluid using a downhole spectrometer. Additionally, the pressure, temperature, density and viscosity of the fluid are concurrently measured.

Figure 4A:
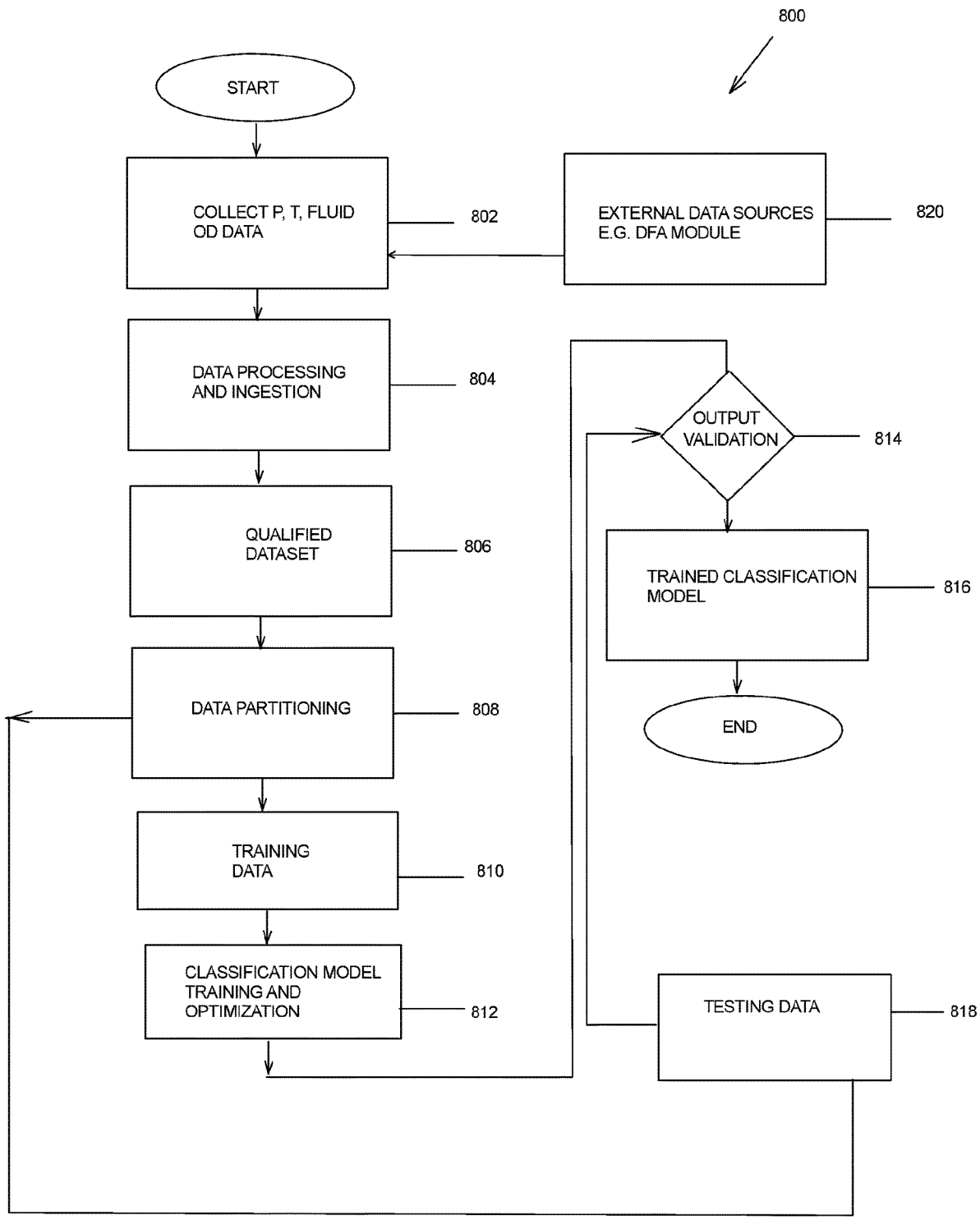
FIG. 4A is a method/workflow for performance of fluid type identification from downhole fluid analysis using machine learning techniques, wherein data extraction and contextualization and model training and validation are described.
Figure 4B:
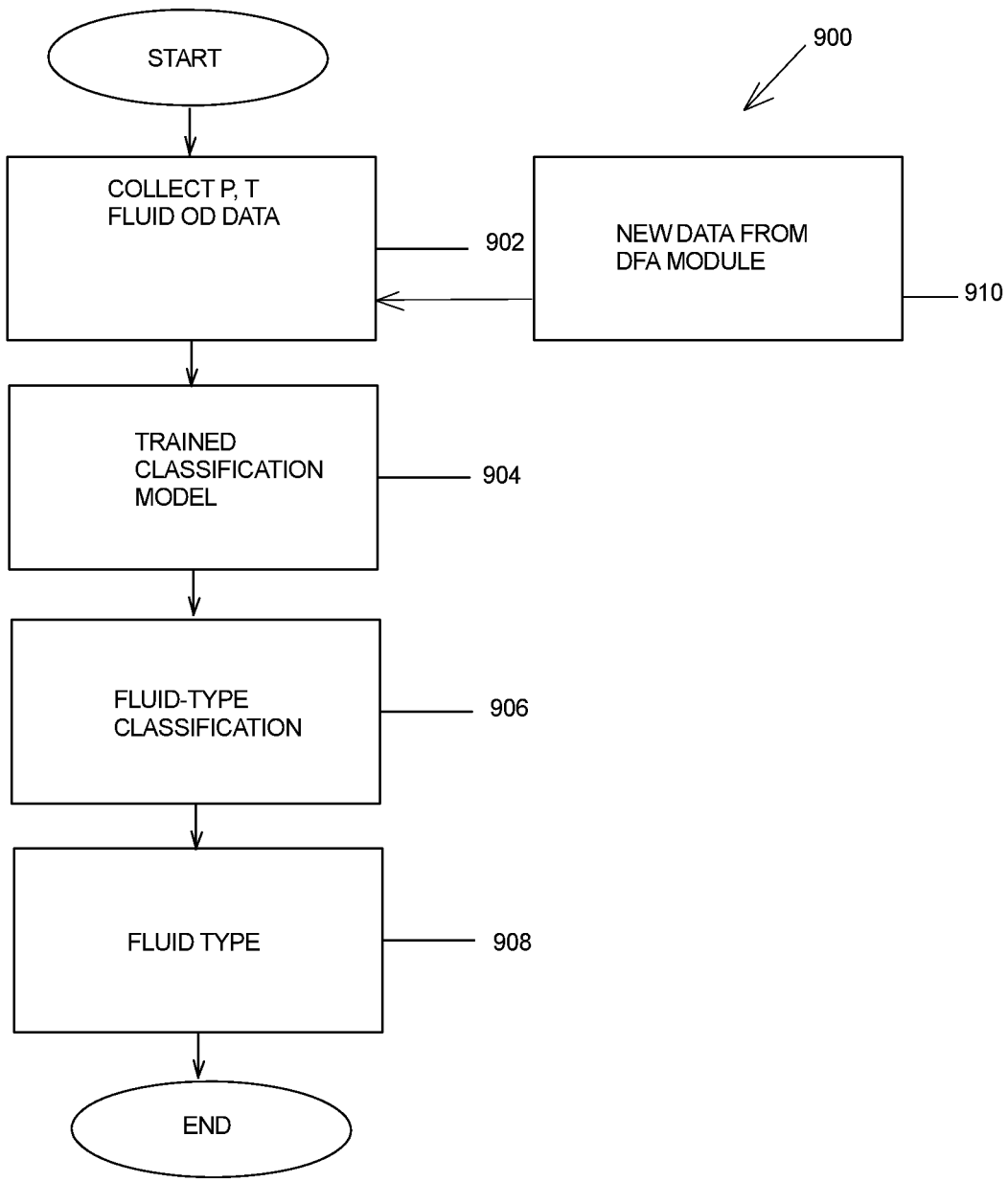
FIG. 4B is a method/workflow for performance of fluid type identification from a trained model using data from downhole sensors.

In embodiments, namely FIGS. 4A and 4B, methods are described where the above-mentioned measurements are used to estimate other physical properties of the formation fluid that cannot be directly measured. Such real-time fluid property estimation enable a user to build a preliminary model of the reservoir fluid during the exploration phase of a hydrocarbon recovery project.

Figure 1C:
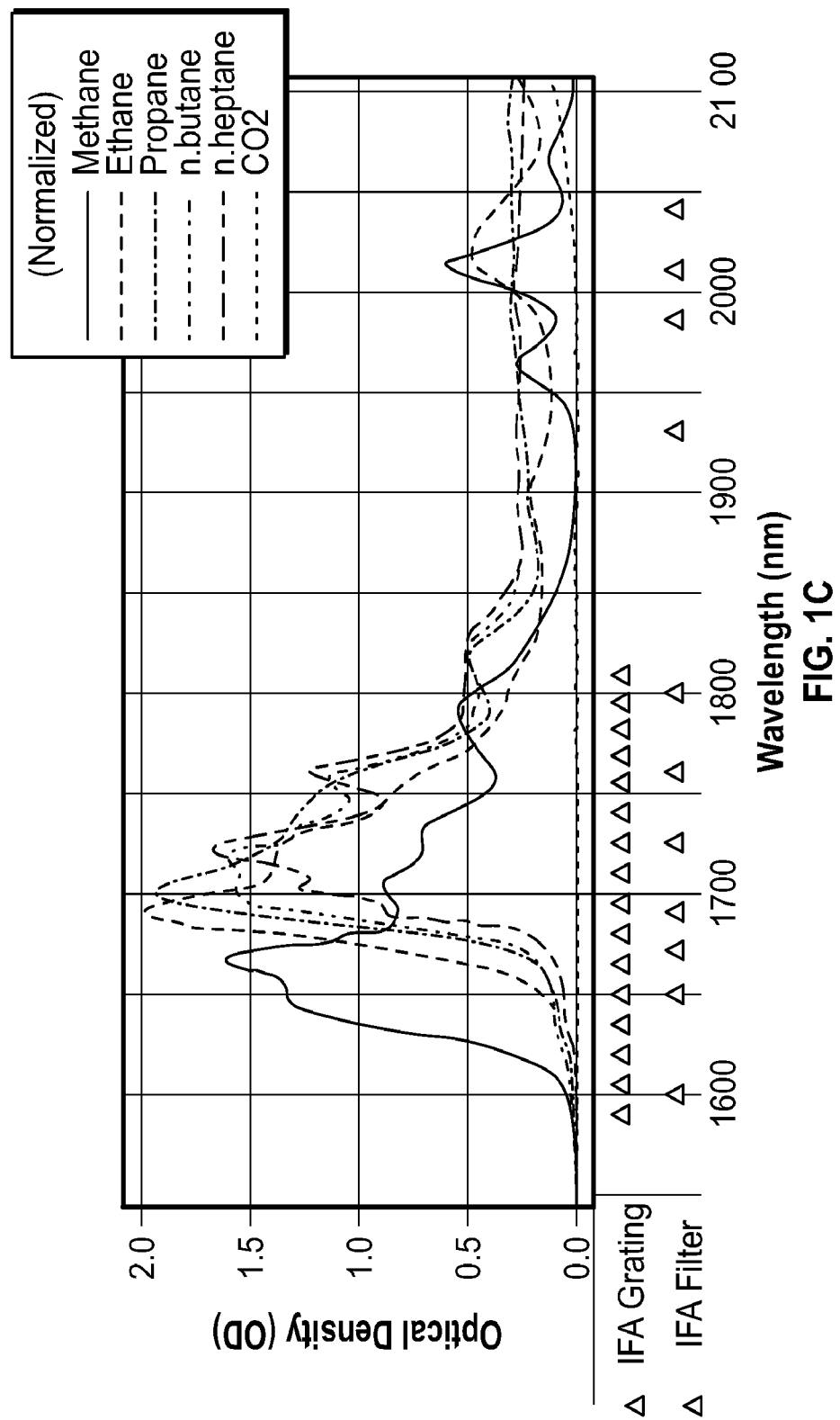
FIG. 1C is a schematic of optical spectrum of multiple alkanes and carbon dioxide over a range 1550 to 2100 nm wavelengths.

The optical module collects optical information of the fluid in the flow line using the downhole spectrometer. The spectrometer measures optical absorbance of the fluid at multiple wavelengths as shown in FIG. 1B. A schematic of optical spectrum of several alkanes and carbon dioxide over a range of wavelengths (1550-2100 nm) is shown in FIG. 1C. These optical spectra are processed to identify the fluid type and to quantify the weight fraction of hydrocarbons (methane, ethane, propane, n-butane, n-pentane, and hexane plus) and carbon dioxide in the fluid. In the example provided, these optical spectra will be used for further characterization, as described in FIGS. 4A and 4B. In FIG. 1C, the methane graph is provided as the left-most data, following by ethane, propane, n-butane, n-heptane and CO2.

We have developed a data-driven workflow where we use the optical characteristics of the fluid alongside pressure, temperature, and composition to estimate fluid-type classification. In this disclosure we demonstrate the use of advanced statistical learning tools to build a classification model to accurately identify the fluid-type with a given set of input parameters. Statistical learning refers to a wide range of tools for exploring and understanding data through statistical models. Models are used for estimating/predicting an output based on one or more inputs.

A database containing fluid properties of prior reservoir fluids was used to build, train, and test the statistical models. Exploratory data analysis techniques were used to identify a set of relevant input parameters for the model. Input parameters were selected based on their respective influence on the output of the model. These statistical tools provide means to connect the distinct measurements from the DFA sensor module to physical properties of the reservoir fluid.

Here examples of the fluid-type identification workflow based on DFA tool measurements are provided using the systems and methods described.

Fluid-Type Identification:

Data extraction and contextualization: In the described embodiment, a database is used containing data such as reservoir pressure (P) and temperature ($T_{res}$), fluid type (oil, gas condensate, gas), composition ($C_1$, $C_2$, $C_3$, $C_4$, $C_5$, $C_{6+}$, $CO_2$ wt %), fluid optical spectra (OD) at specific wavelengths, etc. To ensure data consistency, statistical tools are used (e.g., Mahalanobis distance, Manhattan distance) to identify and remove outliers from the database. Composition mass balance was also checked for the samples. For fluid-type identification, fluid optical spectra were used as the input (predictors) to the classification model. Optical absorbance measurements were extracted from channels corresponding to 1600, 1650, 1671, 1690, 1725, 1760, 1800, 1930, 1985, 2010, and 2040 nm wavelengths on the DFA optical module. The output of the model was a categorical variable (response variable) corresponding to 1 of the 3 fluid types. Other wavelengths can also be used for fluid-type classification.

Figure 2A:
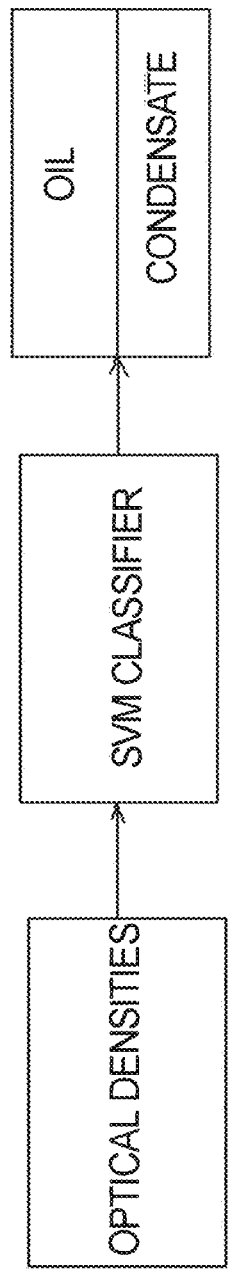
FIG. 2A is a schematic of a diagram of a training of a support-vector-machine classifier model.
Figure 2B:
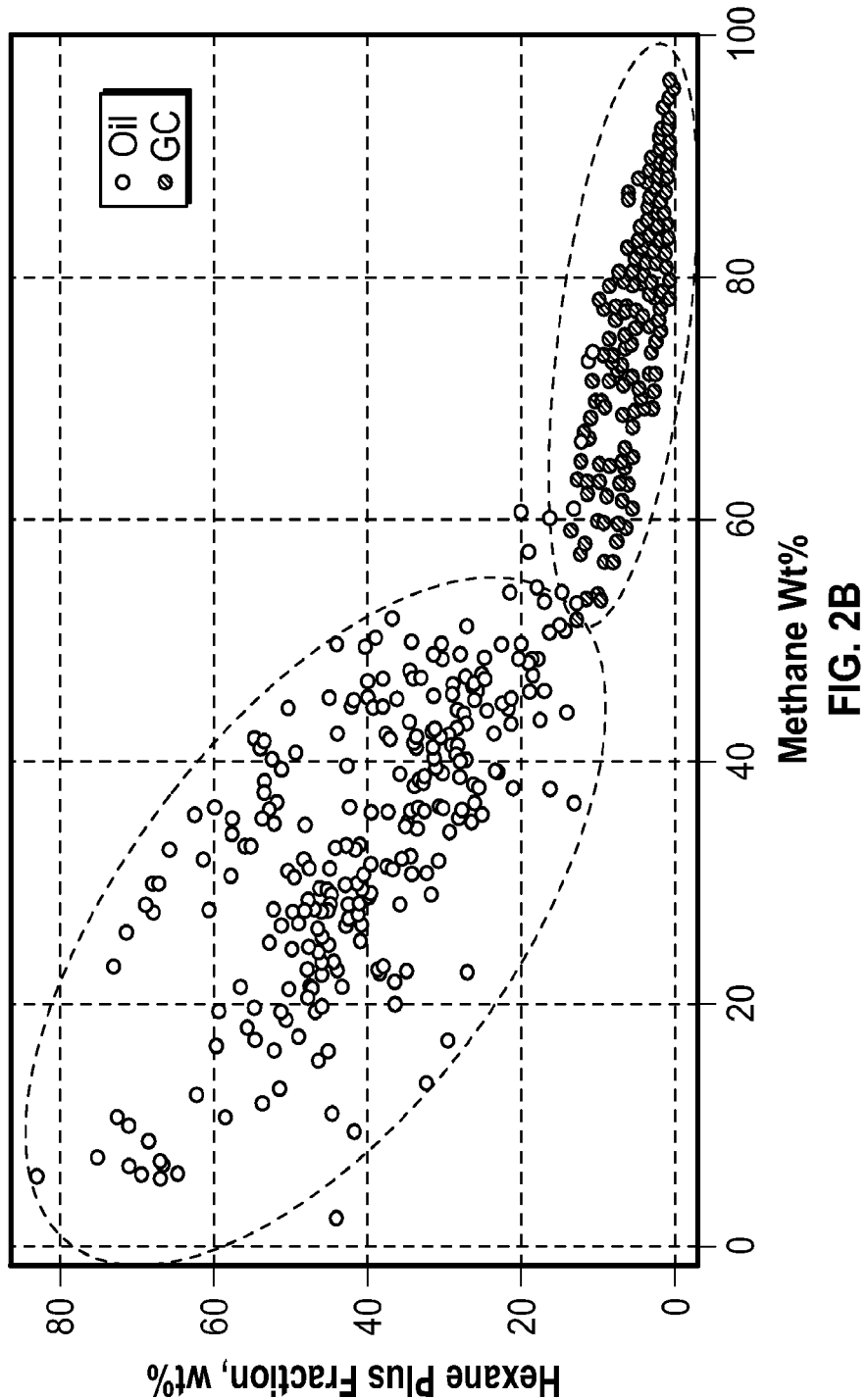
FIG. 2B is a diagram of a fluid identification for fluids obtained from a wellbore.

Model selection and training: A Support Vector Machine (SVM) algorithm is selected as the classification model due to its superior performance with this dataset. The SVM algorithm determines the clusters by identifying maximum separation boundary between the fluid classes in the multi-dimensional space defined by the input parameters. An example of fluid-type identification is shown in FIG. 2B, where the fluid samples are grouped into 2 clusters, namely, black oils and gas condensates. Oil condensates are located in the grouping to the left and higher, while gas condensates are located lower and to the right.

Figure 3A:
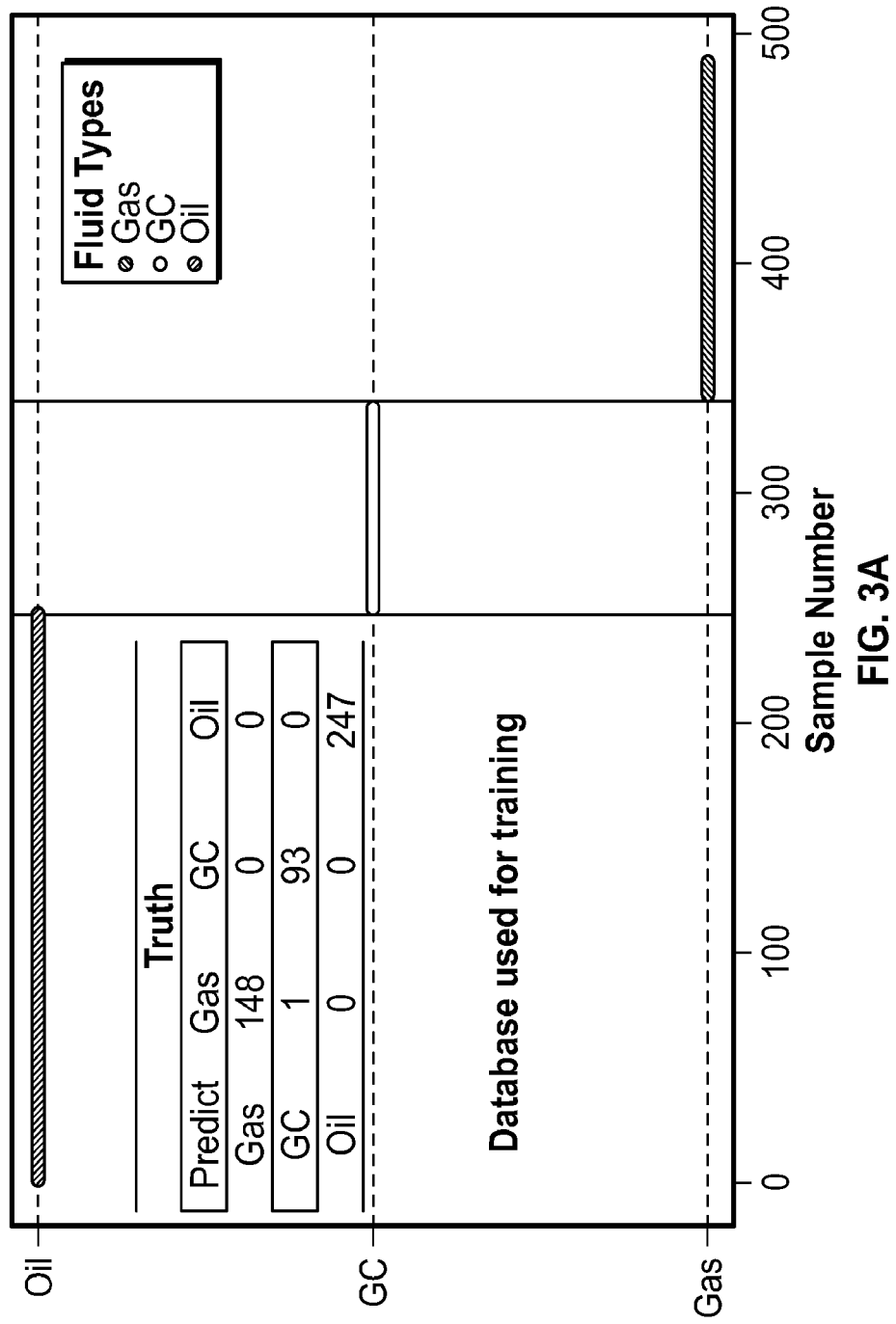
FIG. 3A is a diagram of a learning performance model in one example embodiment of the disclosure.

In this example, a database is used containing 541 samples of black oil, gas condensate (GC), and dry gas type fluids. For training purposes, 489 samples were separated into a training set. A radial kernel was used and trained the model using 10-fold cross-validation. The radial kernel parameters (gamma and cost) were optimized for best performance. The learning performance of the trained model is shown in FIG. 3A. The inset shows the summary of the training results. The trained model was able to identify all the oils and gas condensates; but misclassified 1 dry gas sample as gas condensate. The trained classification model was saved for testing samples not previously seen by the model.

Figure 3B:
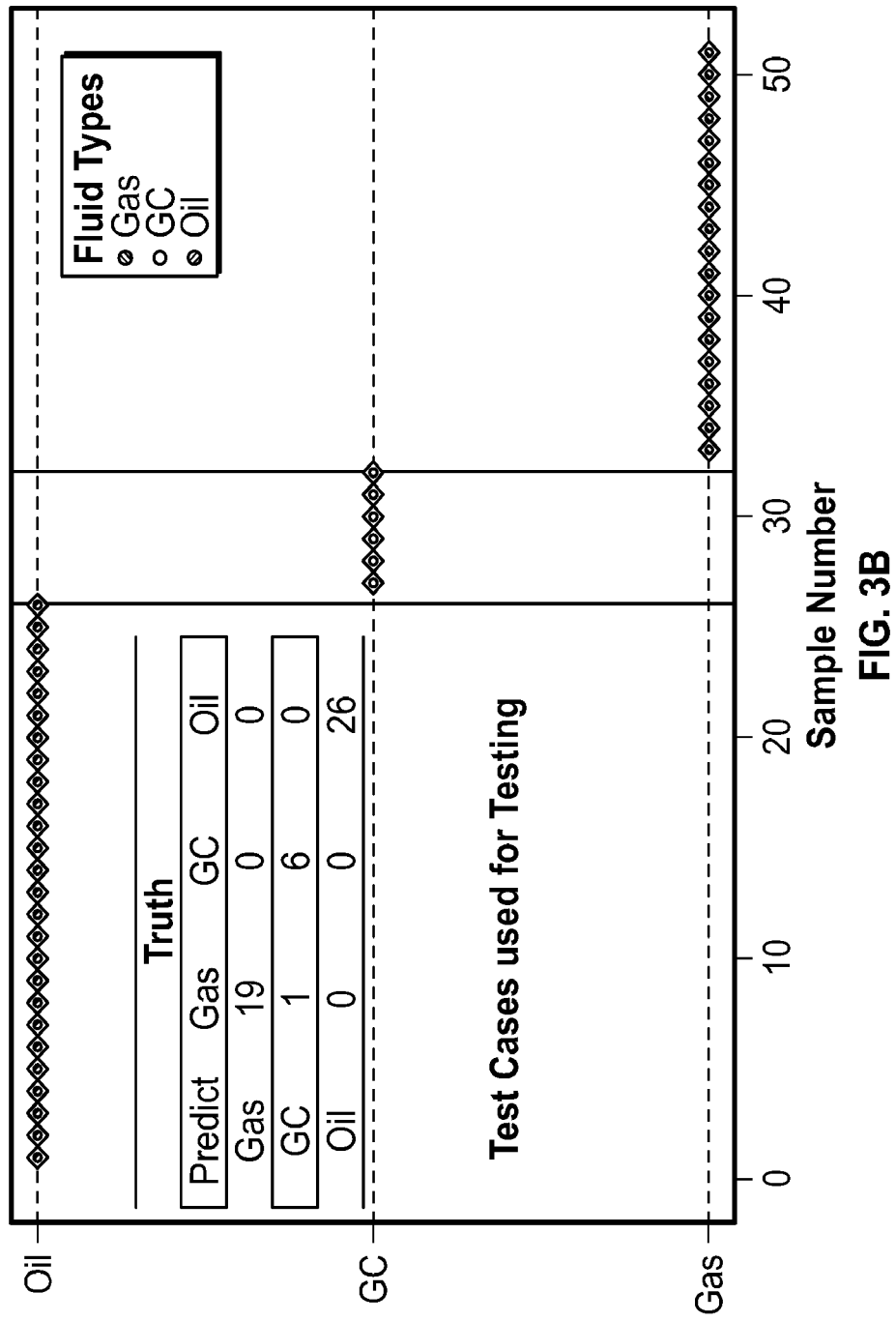
FIG. 3B is a diagram of a learning performance model during testing of a dataset containing black oil, gas condensate and dry gas.

Model testing: The performance of the trained model was tested using another dataset containing 52 fluid samples. These samples were not used for model training. The results are shown in FIG. 3B. All the samples were correctly classified. The classification accuracy of this model was 1.0 on the test data.

For each sample prediction, the SVM model also provides a set of probabilities of belonging to each class of the response variable. Other classification algorithms such as decision tree, gradient boosting, neural nets, etc. or an ensemble of algorithms can also be used for fluid-type classification. Different input features may be selected for another training set. Depending on the training data, a new set of optical absorbance measurements can be used as input to the model.

Aspects of the disclosure also provide methods that may be performed to achieve a stated goal, including controlling components described in the specification. In some embodiments, the methods described may be performed by circuits and/or computers that are configured to perform such tasks.

The general workflow or methods used in this example is summarized in the flowcharts shown in FIGS. 4A and 4B. The flowchart in FIG. 4A is divided into 2 parts, namely, Data Extraction & Contextualization, which includes all steps, except for step 816 Model Training & Validation. The individual blocks in these parts correspond to the steps followed in the example.

The flowchart in FIG. 4B shows the use of the trained model in identifying the fluid-type of a new fluid. The new fluid data (OD, P, $T_{res}$) is used as input to the trained model to classify the new fluid in 1 of the 3 classes (oil, condensate, gas). Once the validity of the classification is established, the test data can be added to the training set to enrich the model. The flowchart in FIG. 4A must be re-executed to update the model. This workflow can also be extended to include other subclasses such as light oil, medium oil, heavy oil, volatile oil etc. In this example, we have only used the OD data of fluids from the currently available database for model training.

It should be noted that apart from the SVM algorithm used in this example, other statistical learning algorithms can be implemented in this workflow if needed. The model selection is guided by the features in the training data. A supervised learning approach was used here. However, this workflow can be extended further by including unsupervised learning algorithms.

Figure 5:
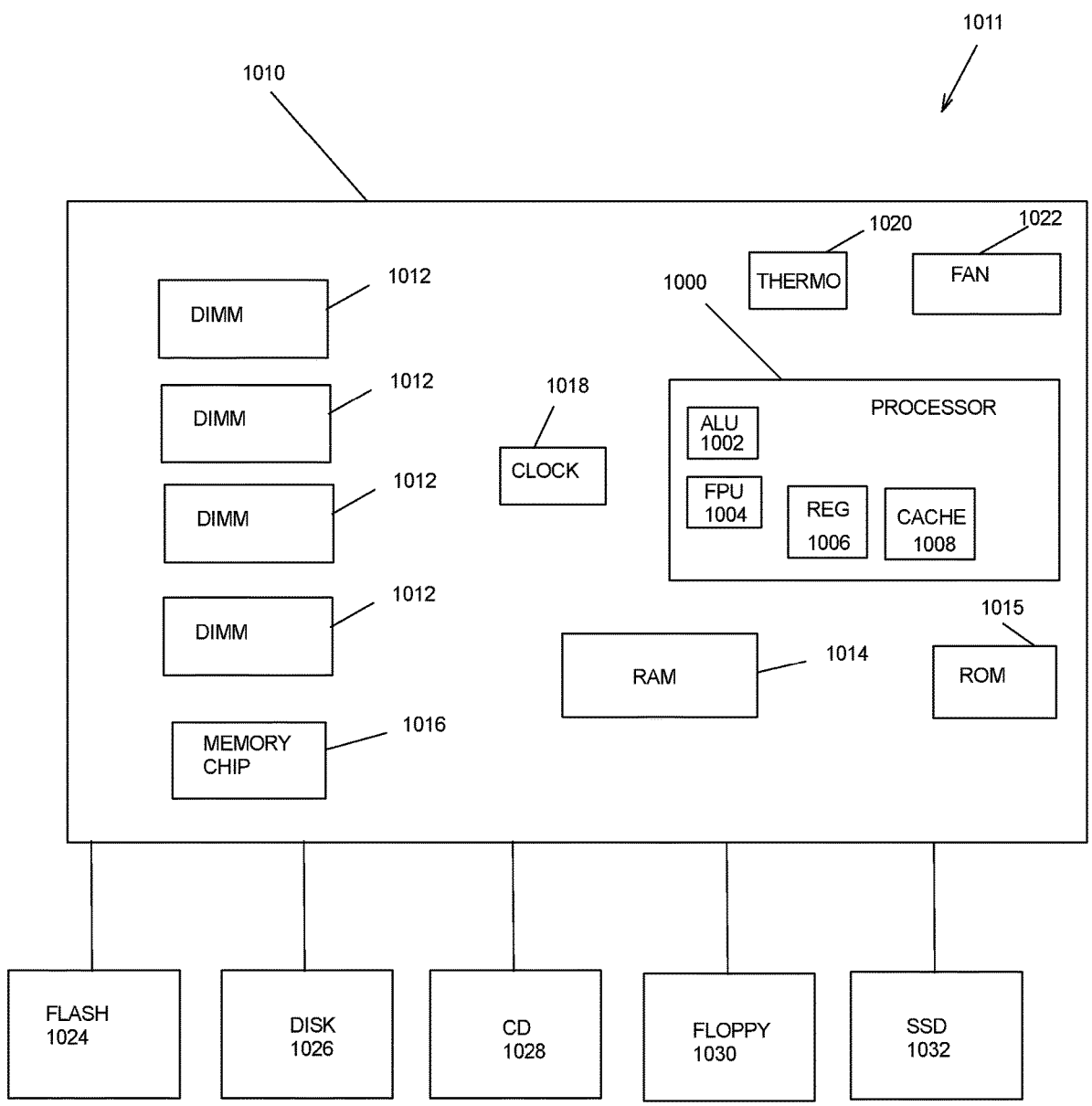
FIG. 5 is an illustration of a computer system that may perform operations as described in relation to FIGS. 4A and 4B.

Referring to FIG. 4A, a method 800 for estimating fluid properties with data from downhole sensors is presented. At 802, different features or measurements of fluid from downhole are obtained. These may include pressure, temperature and other data obtained from an optical analysis. At 820, external data pertaining to fluids may also be obtained. This data may be obtained, for example, from databases. At 804, data is processed and ingested by the method. The method may be performed, for example, on a computer, as illustrated in FIG. 5. From the data above, it is sorted into a qualified data set at 806. At 808, data is partitioned into a training data flow at 810, and testing data at 818. If testing data at 818, the method then continues to 814. If training data, at 810, a classified model training and optimization strategy is performed at 812. After performance at 812, output validation is performed at 814. Validation may check the results obtained from previous steps to expected results. These expected results may include a range of values that would be considered acceptable from an expected error or variance analysis. If values are outside of such expected values, results may be highlighted for a user to evaluate. After 814, at 816, the trained classification model is updated at 816.

Referring to FIG. 4B, a fluid type identification method 900 is illustrated. The method 900 may include collecting pressure, temperature and other optical data at 902. The data may be obtained while sampling downhole through a probe, as previously described. New data from a DFA module may be obtained at 910. Such data may be any type of data that is capable of calculation by a DFA module. The method then progresses to 904, where the data is distributed to the trained classification model. The trained classification model may be data that is provided and updated/trained, resulting from 816. The data is processed using the model to obtain a fluid type classification at 906. At 908, the fluid type may be identified based upon the classification obtained at 906.

In such embodiments, referring to FIG. 5, a computing apparatus 1011 used in the control of equipment and methods previously described is illustrated. In FIG. 5, a processor 1000 is provided to perform computational analysis for instructions provided. The instruction provided, code, may be written to achieve the desired goal and the processor 1000 may access the instructions. In other embodiments, the instructions may be provided directly to the processor 1000.

In other embodiments, other components may be substituted for generalized processors. These specifically designed components, known as application specific integrated circuits ("ASICs") are specially designed to perform the desired task. As such, the ASICs generally have a smaller footprint than generalized computer processors. The ASICs, when used in embodiments of the disclosure, may use field programmable gate array technology, which allows a user to make variations in computing, as necessary. Thus, the methods described herein are not specifically held to a precise embodiment, rather alterations of the programming may be achieved through these configurations.

In embodiments, when equipped with a processor 1000, the processor may have arithmetic logic unit ("ALU") 1002, a floating-point unit ("FPU") 1004, registers 1006 and a single or multiple layer cache 1008. The arithmetic logic unit 1002 may perform arithmetic functions as well as logic functions. The floating-point unit 1004 may be math coprocessor or numeric coprocessor to manipulate number for efficiently and quickly than other types of circuits. The registers 1006 are configured to store data that will be used by the processor 1000 during calculations and supply operands to the arithmetic logic unit 1002 and store the result of operations. The single or multiple layer caches 1008 are provided as a storehouse for data to help in calculation speed by preventing the processor 1000 from continually accessing random-access memory ("RAM") 1014.

Aspects of the disclosure provide for the use of a single processor 1000. Other embodiments of the disclosure allow the use of more than a single processor. Such configurations may be called a multi-core processor where different functions are conducted by different processors to aid in calculation speed. In embodiments, when different processors are used, calculations may be performed simultaneously by different processors, a process known as parallel processing.

The processor 1000 may be located on a motherboard 1010. The motherboard 1010 is a printed circuit board that incorporates the processor 1000 as well as other components helpful in processing, such as memory modules ("DIMMS") 1012, random-access memory 1014, read-only memory 1015, non-volatile memory chips 1016, a clock generator 1018 that keeps components in synchronization, as well as connectors for connecting other components to the motherboard 1010. The motherboard 1010 may have different sizes according to the needs of the computer architect. To this end, the different sizes, known as form factors, may vary from sizes from a cellular telephone size to a desktop personal computer size. The motherboard 1010 may also provide other services to aid in functioning of the processor, such as cooling capacity. Cooling capacity may include a thermometer 1020 and a temperature-controlled fan 1022 that conveys cooling air over the motherboard 1010 to reduce temperature.

Data stored for execution by the processor 1000 may be stored in several locations, including the random-access memory 1014, read-only memory 1015, flash memory 1024, computer hard disk drives 1026, compact disks 1028, floppy disks 1030 and solid-state drives 1032. For booting purposes, data may be stored in an integrated chip called an EEPROM, that is accessed during start-up of the processor. The data, known as a Basic Input/Output System ("BIOS"), contains, in some example embodiments, an operating system that controls both internal and peripheral components.

Different components may be added to the motherboard or may be connected to the motherboard to enhance processing. Examples of such connections of peripheral components may be video input/output sockets, storage configurations (such as hard disks, solid state disks, or access to cloud-based storage), printer communication ports, enhanced video processors, additional random-access memory and network cards.

The processor and motherboard may be provided in a discrete form factor, such as personal computer, cellular telephone, tablet, personal digital assistant or other component. The processor and motherboard may be connected to other such similar computing arrangement in networked form. Data may be exchanged between different sections of the network to enhance desired outputs. The network may be a public computing network or may be a secured network where only authorized users or devices may be allowed access.

As will be understood, method steps for completion may be stored in the random-access memory, read-only memory, flash memory, computer hard disk drives, compact disks, floppy disks and solid-state drives.

Different input/output devices may be used in conjunction with the motherboard and processor. Input of data may be through a keyboard, voice, Universal Serial Bus ("USB") device, mouse, pen, stylus, Firewire, video camera, light pen, joystick, trackball, scanner, bar code reader and touch screen. Output devices may include monitors, printers, headphones, plotters, televisions, speakers and projectors.

In one non-limiting embodiment, a method is disclosed. The method may comprise collecting optical spectral data for a downhole fluid. The method may also comprise providing the collected optical spectral data to a trained classification module. The method may also comprise processing the collected optical spectral data with the trained classification module configured to determine a fluid type classification. The method may also comprise determining a fluid type based upon the classification based upon the trained classification module.

In another non-limiting example embodiment, the method may be performed wherein the collecting the optical spectral data is from a downhole system.

In another non-limiting example embodiment, the method may be performed wherein the downhole system is a downhole fluid analysis module.

In another non-limiting example embodiment, the method may be performed wherein the collecting the optical spectral data is performed from a downhole probe.

In another non-limiting example embodiment, the method may further comprise collecting new data from a downhole fluid analysis module prior to collecting at least one of pressure and temperature data.

In another non-limiting example embodiment, the method may be performed wherein the determining the fluid type classification is performed through a support vector machine.

In another non-limiting example embodiment, the method may be performed wherein the support vector machine is configured to identify a fluid type classification based upon an identified maximum separation boundary between fluid classes and comparing the at least one of pressure and temperature data for the downhole fluid to the identified maximum separation boundary.

In another example embodiment, the method may be performed wherein the collected optical spectral data includes at least one of a pressure and temperature of the downhole fluid.

In another example embodiment, a method is disclosed. The method comprises collecting optical data related to a downhole fluid and extracting data from the collected optical data to form a qualified dataset. The method may also provide for partitioning the qualified dataset to determine a portion of the qualified dataset related to testing data and a second portion of the qualified dataset related to training data. The method may also provide for performing a classification model training on the second portion of the qualified dataset related to the training data, resulting in a trained classification model.

In another example embodiment, the method may further comprise performing an output validation after performing the classification model training.

In another example embodiment, the method may further comprise obtaining external data from an external data source related to fluid properties.

In another example embodiment, the method may be performed wherein the obtaining the external data from the external data source is from a downhole fluid analysis module.

In another example embodiment, the method may be performed wherein the downhole fluid analysis module is configured with a filter array spectrometer, a grating spectrometer and a resistivity sensor.

In another example embodiment, the method may be performed wherein the downhole fluid analysis module is configured with one of a density sensor, a viscosity sensor, a pressure gauge, and a temperature gauge.

In another example embodiment, the method may be performed wherein the classification model is categorically variable.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:

1. A method, comprising:
   collecting optical spectral data for a downhole fluid of a wellbore;
   providing the collected optical spectral data to a trained classification module;
   processing the collected optical spectral data with the trained classification module configured to determine a fluid type classification based upon an identified maximum separation boundary between fluid classes and comparing at least one of pressure or temperature data for the downhole fluid to the identified maximum separation boundary;
   determining a fluid type based upon the fluid type classification based upon the trained classification module; and
   controlling components associated with a tool-string in the wellbore based on the determined fluid type.

2. The method according to claim 1, wherein the optical spectral data is collected from a downhole system.

3. The method according to claim 2, wherein the downhole system is a downhole fluid analysis module.

4. The method according to claim 1, wherein the optical spectral data is collected from a downhole probe.

5. The method according to claim 1, further comprising:
   collecting additional data from a downhole fluid analysis module prior to collecting at least one of pressure or temperature data.

6. The method according to claim 1, wherein the fluid type classification is determined through a support vector machine.

7. The method according to claim 1, wherein the collected optical spectral data includes at least one of a pressure or a temperature of the downhole fluid.

8. The method according to claim 1, further comprising:
   collecting optical data related to the downhole fluid;
   extracting data from the collected optical data to form a qualified dataset;
   partitioning the qualified dataset to determine a portion of the qualified dataset related to testing data and a second portion of the qualified dataset related to training data; and
   performing a classification model training on the second portion of the qualified dataset related to the training data, resulting in the trained classification model.

9. The method according to claim 8, further comprising performing an output validation after performing the classification model training.

10. The method according to claim 8, further comprising:
    obtaining external data from an external data source related to fluid properties.

11. The method according to claim 10, wherein the obtaining the external data from the external data source is from a downhole fluid analysis module.

12. The method according to claim 11, wherein the downhole fluid analysis module includes a filter array spectrometer, a grating spectrometer and a resistivity sensor.

13. The method according to claim 11, wherein the downhole fluid analysis module includes one of a density sensor, a viscosity sensor, a pressure gauge, or a temperature gauge.

14. The method according to claim 10, wherein the classification model is categorically variable.

* * * * *